US012589242B2

(12) United States Patent
Kim et al.

(10) Patent No.: US 12,589,242 B2
(45) Date of Patent: Mar. 31, 2026

(54) ELECTRICAL STIMULATION-BASED ANKLE MUSCLE REHABILITATION TRAINING APPARATUS AND CONTROL METHOD THEREOF

(71) Applicant: NATIONAL REHABILITATION CENTER, Seoul (KR)

(72) Inventors: Hogene Kim, Seoul (KR); Joon-Ho Shin, Seoul (KR); Ji-Eun Cho, Seoul (KR)

(73) Assignee: National Rehabilitation Center, Seoul (KR)

( * ) Notice: Subject to any disclaimer, the term of this patent is extended or adjusted under 35 U.S.C. 154(b) by 483 days.

(21) Appl. No.: 18/251,266

(22) PCT Filed: Oct. 5, 2021

(86) PCT No.: PCT/KR2021/013556
§ 371 (c)(1),
(2) Date: May 1, 2023

(87) PCT Pub. No.: WO2022/097933
PCT Pub. Date: May 12, 2022

(65) Prior Publication Data
US 2023/0414937 A1 Dec. 28, 2023

(30) Foreign Application Priority Data
Nov. 5, 2020 (KR) ........................ 10-2020-0147151

(51) Int. Cl.
*A61N 1/00* (2006.01)
*A61N 1/04* (2006.01)
*A61N 1/36* (2006.01)

(52) U.S. Cl.
CPC ....... *A61N 1/36003* (2013.01); *A61N 1/0452* (2013.01); *A61N 1/0492* (2013.01); *A61N 1/3603* (2017.08)

(58) Field of Classification Search
None
See application file for complete search history.

(56) References Cited

U.S. PATENT DOCUMENTS

2010/0160987 A1* 6/2010 Simmons ............. A61H 1/0262
607/3
2020/0367823 A1* 11/2020 Chahine ............... A61B 5/6807

FOREIGN PATENT DOCUMENTS

KR 10-0946186 B1 3/2010
KR 10-2014-0001040 A 1/2014
(Continued)

*Primary Examiner* — William J Levicky
*Assistant Examiner* — Anant A Gupta
(74) *Attorney, Agent, or Firm* — Rabin & Berdo, P.C.

(57) ABSTRACT

An electrical stimulation-based ankle muscle rehabilitation training apparatus comprising: an ankle movement providing device that provides dorsiflexion, plantarflexion, eversion, inversion, supination, and pronation operations; first and second electrode pads respectively attached to the proximal and distal portions of the tibialis anterior representative of the ankle dorsiflexor; third and fourth electrode pads respectively attached to the proximal and distal portions of the peroneus longus representative of the ankle evertor; an electrical stimulation providing unit for applying electrical stimulation to the first to fourth electrode pads; and a control unit that controls the ankle movement providing device to sequentially perform a first operation of repeating dorsiflexion and plantarflexion movements, a second operation of repeating eversion and inversion movements, and a third operation of repeating supination and pronation movements at an appropriate slow speed, and controls the elec- (Continued)

trical stimulation providing unit to apply electrical stimulation to the first to fourth electrode pads.

9 Claims, 8 Drawing Sheets

(56)                         References Cited

FOREIGN PATENT DOCUMENTS

| | | | | |
|---|---|---|---|---|
| KR | 10-1489795 | B1 | 2/2015 | |
| KR | 10-2017-0035830 | A | 3/2017 | |
| KR | 10-2017-0041545 | A | 4/2017 | |
| KR | 10-2019-0073989 | A | 6/2019 | |
| KR | 10-2014536 | B1 | 11/2019 | |
| KR | 20190129469 | A | * 11/2019 | ............. A61B 5/112 |
| KR | 10-2019-0134352 | A | 12/2019 | |

* cited by examiner

Peroneus
longus
muscle

Tibialis
anterior
muscle

ELECTRICAL STIMULATION-BASED ANKLE MUSCLE REHABILITATION TRAINING APPARATUS AND CONTROL METHOD THEREOF

TECHNICAL FIELD

The present disclosure relates to a technology of appropriately controlling an ankle muscle rehabilitation training apparatus to induce a change in the angle of the ankle while applying electric stimulation using an electric pad to a specific part of the leg, thereby improving ankle movement and muscle strength.

BACKGROUND ART

In general, ankle movement, along with the muscle strength, has an important effect on gait stability. The ankle movements can be summarized as movements occurring in the sagittal plane, the frontal plane, and the transverse plane, and occurs according to the movements of the ankle joint (or talocrural joint), transverse tarsal joint, and subtalar joint.

Damage, impairment, and loss of lower extremity function due to musculoskeletal and central nervous system diseases may lead to a decrease in gait ability or loss, which can be regarded as one of the serious causes that hinder performance of independent daily living. In particular, in the case of stroke, which is one of the central nervous system diseases, most of the patients support 61% to 80% of the total body weight with a non-injured lower limb, thus exhibiting asymmetric posture alignment and deterioration of balance ability. Abnormal gait patterns after the stroke include stiff-knee gait during the swing phase, genu recurvatum during the stance phase, reduction of dorsiflexion at the stance phase and excessive plantar flexion during the swing phase, and the like. In addition, gait speed, cadence, and stride length are reduced, and double stance periods are increased, and the standing period of the damaged side is shorter than that of the non-injured side.

Therefore, for the gait rehabilitation of people with central nervous system disorders such as stroke, functional electric stimulation, brace support, and the like are applied, or methods of performing joint movement range exercises by the therapist, stretching exercises, resistance bands, manual ankle trainers, weight-bearing resistance exercises in an upright posture, and so on are clinically used. Furthermore, in order to provide a range of movement of the ankle, an automatic ankle trainer is also used, which includes a rotation shaft corresponding to the ankle joint and driven by a motor. However, these methods have limitations when it comes to improving and rehabilitating ankle function by way of improving sensory function, functional movement, and muscle strength of the ankle.

DETAILED DESCRIPTION OF INVENTION

Technical Problem

An object of the present disclosure is to provide a technology capable of inducing angle change of the ankle and also improving ankle muscle strength by attaching an electrical pad to a certain part of the leg and then appropriately applying electrical stimulation according to an ankle rehabilitation operation.

In addition, another object of the present disclosure is to provide a method for applying electrical stimulation to the muscles by the anatomical biaxial movement of the ankle joint for people with central nervous system damage who have difficulty in voluntary control of the ankle muscles due to clinical characteristics such as muscle weakness, shortness, spasticity, and sensory function deterioration of the ankle muscles.

Technical Solution

The present disclosure provides an electrical stimulation-based ankle muscle rehabilitation training apparatus including: an ankle movement providing device (100) that provides dorsiflexion, plantarflexion, eversion, inversion, supination, and pronation operations; first and second electrode pads (P1, P2) respectively attached to the proximal and distal portions of the tibialis anterior representative of the ankle dorsiflexor; third and fourth electrode pads (P3, P4) respectively attached to the proximal and distal portions of the peroneus longus representative of the ankle evertor; an electrical stimulation providing unit for applying electrical stimulation to the first to fourth electrode pads; and a control unit that controls the ankle movement providing an apparatus to sequentially perform a first operation of repeating dorsiflexion and plantarflexion movements a plurality of times, a second operation of repeating eversion and inversion movements a plurality of times, and a third operation of repeating pronation and supination movements a plurality of times, and controls the electrical stimulation providing unit to apply electrical stimulation to the first to fourth electrode pads.

The control unit may control so as to apply electrical stimulation to the first and second electrode pads (P1, P2) when the dorsiflexion movement occurs during the first operation, apply electrical stimulation to the third and fourth electrode pads (P3, P4) when the inversion movement occurs during the second operation, and apply electrical stimulation to the first to fourth electrode pads (P1, P2, P3, P4) when the supination movement occurs during the third operation, and apply the electrical stimulation to none of the first to fourth electrode pads when the plantar flexion movement occurs during the first operation, when the eversion movement occurs during the second operation, and when the pronation movement occurs during the third operation.

It is desirable that, in the above first operation, the dorsiflexion and plantar flexion movements repeat 20 times in sequence, in the second operation, the inversion and eversion movements repeat 20 times in sequence, and in the third operation, the supination and pronation movements repeat 40 times in sequence. It is also desirable that all movements are performed at an appropriately slow speed (e.g., 2.14°/sec) in consideration of occurrence of speed-dependent spasticity of patients with central nervous system damage, and it is also desirable that the time required for one operation of the dorsiflexion movement is 10 to 12 seconds, and the time required for one operation of each of the plantar flexion, eversion, inversion, supination, and pronation movements is 10 to 15 seconds.

Effects of Invention

According to the present disclosure, using the ankle muscle training apparatus, it is possible to induce change in the angle of the ankle such as dorsiflexion, plantar flexion, inversion, eversion, supination, and pronation, while applying electrical stimulation to a certain muscle part of the leg through an electrical pad, and with the biaxial ankle movement provided by the ankle muscle training apparatus and the electrical stimulation, there are effects that the range of motion of the ankle joint of a user with central nervous system damage can be improved, pain can be relieved, and ankle sensation and exercising function can be improved, and it is also expected that balance and ankle control ability in the daily life such as walking can be improved.

BEST MODE FOR EMBODYING INVENTION

The objectives, specific advantages and novel features of the present disclosure will become more apparent from the following detailed description and the preferred embodiments, which are associated with the accompanying drawings. In addition, terms described herein are terms defined in consideration of functions in the present disclosure, which may vary according to the intention or convention of a user or an operator. Therefore, definitions of these terms should be made based on the contents throughout the present specification.

Figure 1:
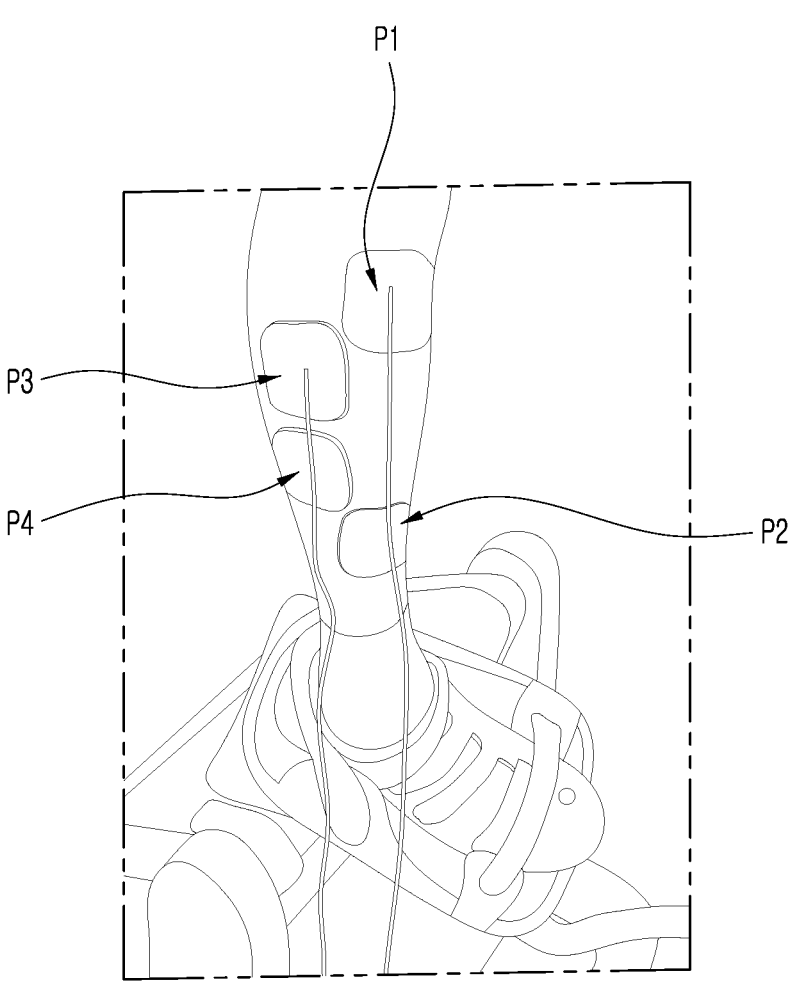
FIG. 1 illustrates an ankle muscle rehabilitation training apparatus with an electrode pad attached to a certain part of the leg according to an embodiment.
Figure 2:
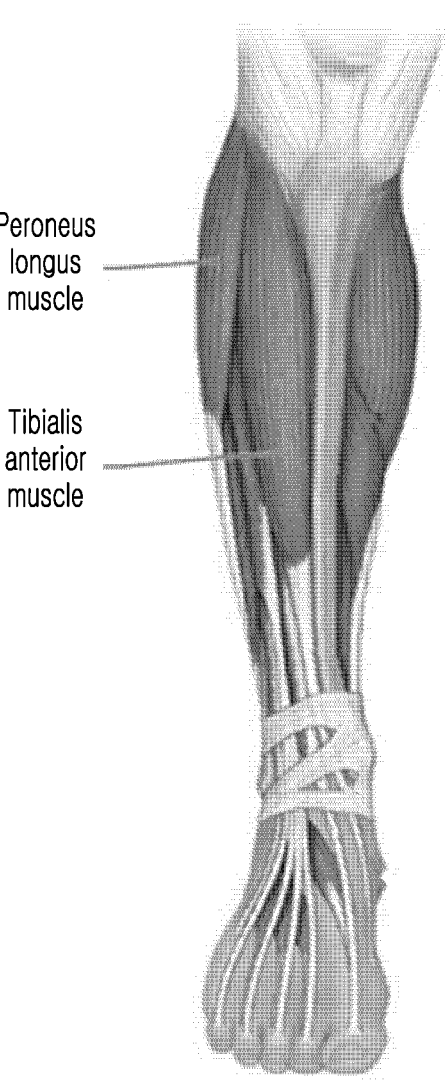
FIG. 2 provides anatomical data of the muscles, indicating portions where the electrode pads are attached according to the disclosure.
Figure 3:
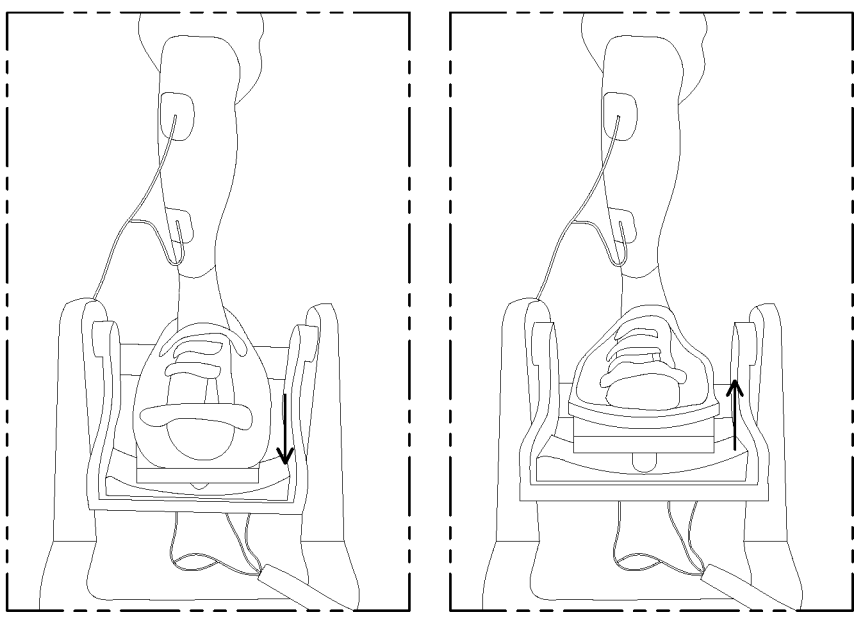
FIG. 3 illustrates dorsiflexion and plantar flexion movements being performed using an ankle muscle rehabilitation training apparatus according to an embodiment of the disclosure.
Figure 4:
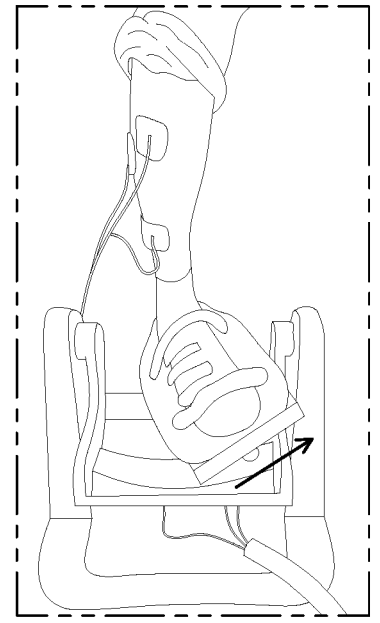
FIG. 4 illustrates eversion and inversion movements being performed using an ankle muscle rehabilitation training apparatus according to an embodiment of the disclosure.
Figure 4:
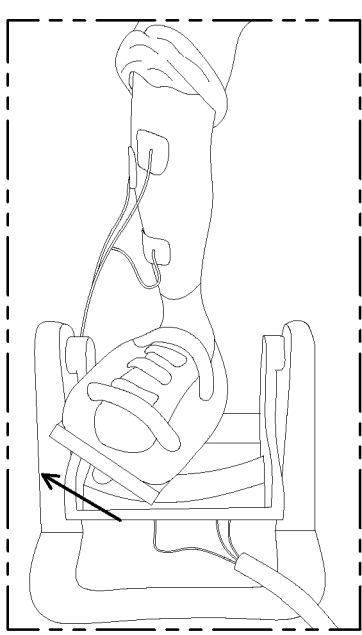
Figure 5:
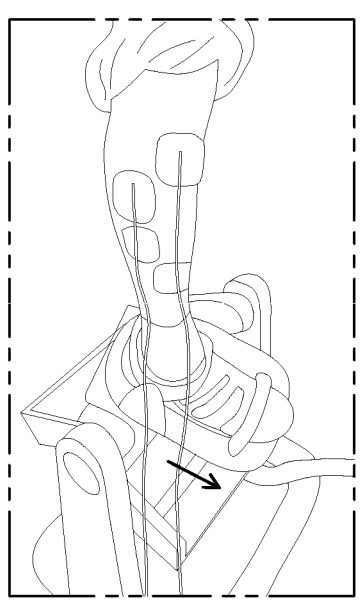
FIG. 5 illustrates supination and pronation movements being performed using an ankle muscle rehabilitation training apparatus according to an embodiment of the disclosure.
Figure 5:
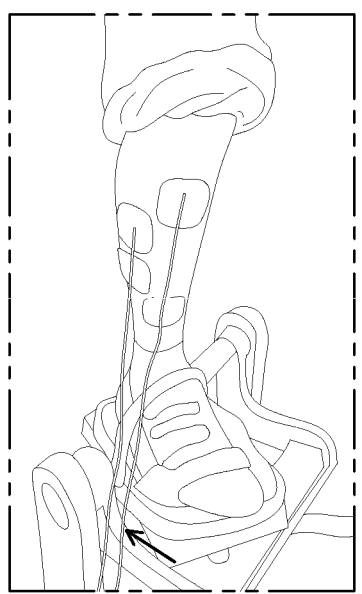
Figure 6:
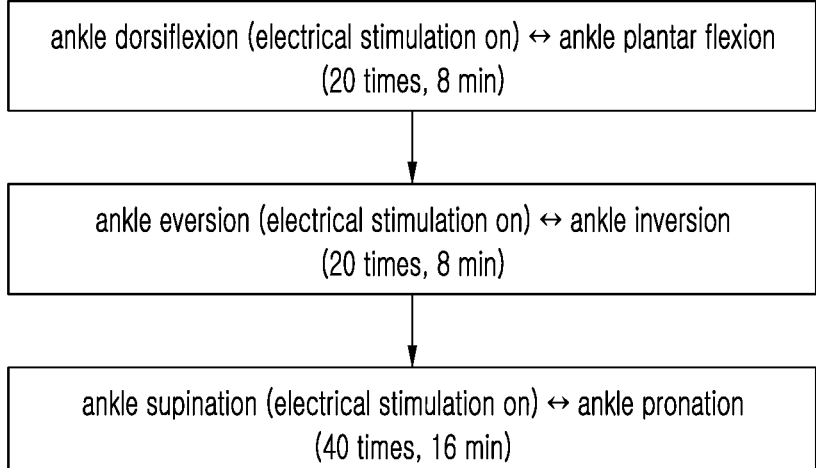
FIG. 6 illustrates an example of a training protocol using an ankle muscle rehabilitation training apparatus according to an embodiment of the disclosure.
Figure 7:
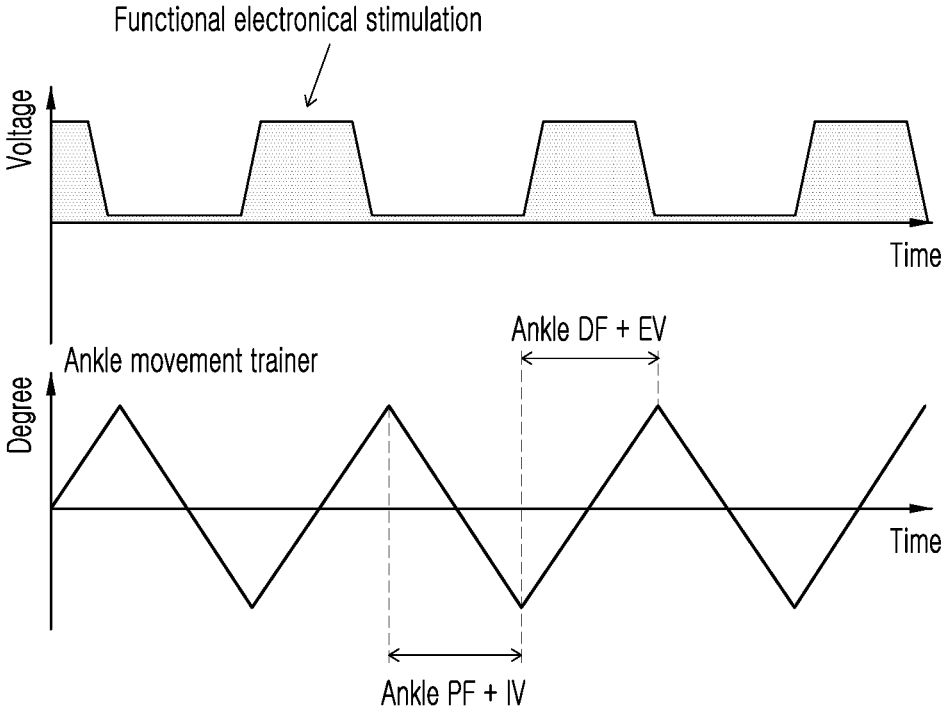
FIG. 7 illustrates an exemplary graph showing a voltage applied to an electrode pad and an amount of change in the angle of an ankle during a training process of using an ankle muscle rehabilitation training apparatus according to an embodiment of the disclosure.

FIG. 1 illustrates an ankle muscle rehabilitation training apparatus with an electrode pad attached to a certain part of the leg according to an embodiment of the disclosure, FIG. 2 provides anatomical data of the muscles, indicating portions where the electrode pads are attached according to the disclosure, FIG. 3 illustrates dorsiflexion and plantar flexion movements being performed using an ankle muscle rehabilitation training apparatus according to an embodiment of the disclosure, FIG. 4 illustrates eversion and inversion movements being performed using an ankle muscle rehabilitation training apparatus according to an embodiment of the disclosure, FIG. 5 illustrates supination and pronation movements being performed using an ankle muscle rehabilitation training apparatus according to an embodiment of the disclosure, FIG. 6 illustrates an example of a training protocol using an ankle muscle rehabilitation training apparatus according to an embodiment of the disclosure, and FIG. 7 illustrates an exemplary graph showing a voltage applied to an electrode pad and an amount of change in the angle of an ankle during a training process of using an ankle muscle rehabilitation training apparatus according to an embodiment of the disclosure.

[Control Algorithm Using Ankle Muscle Rehabilitation Training Apparatus]

First, the ankle muscle rehabilitation training apparatus according to the disclosure is configured such that it includes an ankle movement providing device 100 that provides the ankle with dorsiflexion, plantar flexion, eversion, inversion, supination, and pronation operations. Specific hardware configuration of the ankle movement providing device will be separately described in detail below.

In addition, the ankle muscle rehabilitation training apparatus of the present disclosure includes first to fourth electrode pads (P1, P2, P3, P4) attached to the leg and applies electrical stimulation thereto, an electrical stimulation providing unit (not shown) providing electrical stimulation to the first to fourth electrode pads, and a control unit that controls the ankle movement providing device 100 and the electrical stimulation providing unit.

Referring to FIGS. 1 and 2, the first and second electrode pads (P1, P2) are attached to the proximal and distal portions of the tibialis anterior representative of the ankle dorsiflexor, respectively. Further, the third and fourth electrode pads (P3, P4) are attached to the proximal and distal portions of the peroneus longus representative of the ankle evertor, respectively.

FIG. 2 shows the positions of the tibialis anterior muscle and peroneus longus muscle in yellow, and FIG. 1 shows the electrode pads attached to the proximal and distal portions of these.

While it is described above by way of an example that the first and second electrode pads (P1, P2) are attached to the tibialis anterior muscle, the first and second electrode pads (P1, P2) may be attached to the ankle dorsiflexor rather than the tibialis anterior muscle. That is, the first and second electrode pads (P1, P2) may preferably attached to the tibialis anterior muscle, which is representative of the ankle dorsiflexor muscles, but not necessarily limited to the tibialis anterior muscle.

In addition, while it is described by way of an example that the third and fourth electrode pads (P3, P4) are attached to the peroneous longus muscle, the third and fourth electrode pads (P3, P4) may be attached to the ankle evertor muscle rather than the peroneous longus muscle. That is, the third and fourth electrode pads (P3, P4) may preferably be attached to the peroneous longus muscle, which is a representative among evertors, but not necessarily limited to the peroneous longus muscle.

Further, the control unit operates the ankle movement providing device to perform various operations with respect to the ankle. Specifically, the control unit controls the ankle movement providing device to sequentially perform a first operation of repeating dorsiflexion and plantar flexion movements a plurality of times, a second operation of repeating eversion and inversion movements a plurality of times, and a third operation of repeating supination and pronation movements a plurality of times.

The control unit controls the electrical stimulation providing unit so that electrical stimulation is applied to any one or all of the first to fourth electrode pads when a certain operation of the ankle movement operations is performed.

FIG. 3 shows the first operation, i.e., the dorsiflexion and plantar flexion movements, FIG. 4 shows the second operation, i.e., the eversion and inversion movements, and FIG. 5 shows the third operation, i.e., the supination and pronation movements, respectively.

According to the present disclosure, the electrical stimulation is applied such that the electrical stimulation is applied to the first and second electrode pads (P1, P2) only when the dorsiflexion movement occurs during the process of the first operation. Further, the electrical stimulation is applied to the third and fourth electrode pads (P3, P4) only when the eversion movement occurs during the second operation. Further, the electrical stimulation is applied to the first to fourth electrode pads (P1, P2, P3, P4) only when the supination movement occurs during the third operation.

That is, in the present disclosure, the electrical stimulation is applied to none of the first to fourth electrode pads when the plantar flexion movement occurs during the first operation, when the eversion movement occurs during the second operation, and when the pronation movement occurs during the third operation.

In addition, for the number and time of the first to third operations according to the disclosure, it is preferable that the first operation performs the dorsiflexion and plantar flexion movements 20 times in sequence, the second operation performs the eversion and inversion movements 20 times in sequence, and the third operation performs the supination and pronation movements 40 times in sequence. In addition, it is desirable that the time required for one operation of the dorsiflexion movement is 10 to 12 seconds, and the time required for one operation of each of the plantar flexion, eversion, inversion, supination, and pronation movements is 10 to 15 seconds.

For the degree of the ankle movement, 80% of the individual's maximum range of joint movement is applied, and for the time of each ankle movement, different time may be applied per person. It is desirable that the ankle movement is performed at an appropriately slow speed (e.g., 2.14°/sec) in consideration of the occurrence of speed-dependent spasticity of the patient with central nervous system damage (the possibility of occurrence of spasticity increases as the movement speed increases). It is desirable that the total application time is limited to about 30 minutes for the ankle movement training in consideration of muscle fatigue due to continuous electrical stimulation.

Through the process described above, the present disclosure provides biaxial ankle movement training for the patient with central nervous system damage, and provides biaxial ankle movement according to the subtalar joint and talocrural joint of the ankle and corresponding electrical stimulation to the ankle. That is, the biaxial ankle movement includes dorsiflexion, plantar flexion, inversion, eversion, pronation, and supination of the ankle, and the ankle muscle training apparatus according to the disclosure may provide passive biaxial ankle joint movement at a constant speed according to the range of motion of the joint of a user.

According to the present disclosure, for the time of applying the electrical stimulation, the electrical stimulation is applied to the ankle muscles for the ankle training during the dorsiflexion, eversion, and supination movements of the ankle, including ramp-up and ramp-down of the electrical stimulation, and applied to the corresponding muscles (tibialis anterior, peroneus longus) that causes each movement according to the biaxial ankle movement.

With the training process described above, the present disclosure improves the ability of controlling the ankle muscle by applying not only the ankle movement, but also the electrical stimulation to the ankle muscle having difficulty of the voluntary ankle muscle control due to problems such as weakness and stiffness of the ankle muscles.

[Hardware Structure of Ankle Muscle Rehabilitation Training Apparatus]

Hereinafter, configuration of the ankle movement providing device 100 as a device for providing a control method, which is the training providing algorithm described above, will be described.

Figure 8:
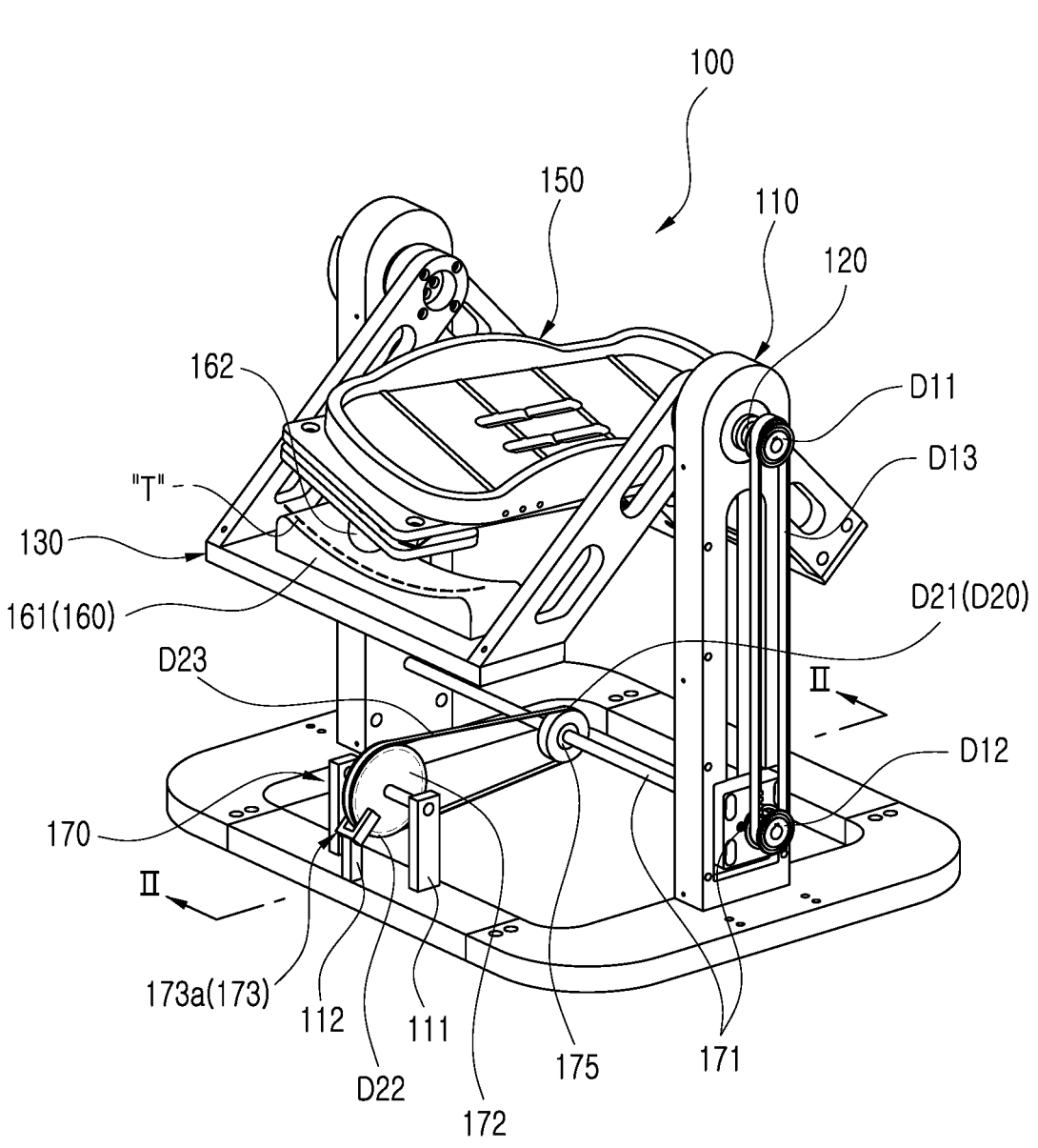
FIG. 8 is a perspective view schematically illustrating an ankle movement providing device in an ankle muscle rehabilitation training apparatus according to an embodiment of the disclosure.
Figure 9:
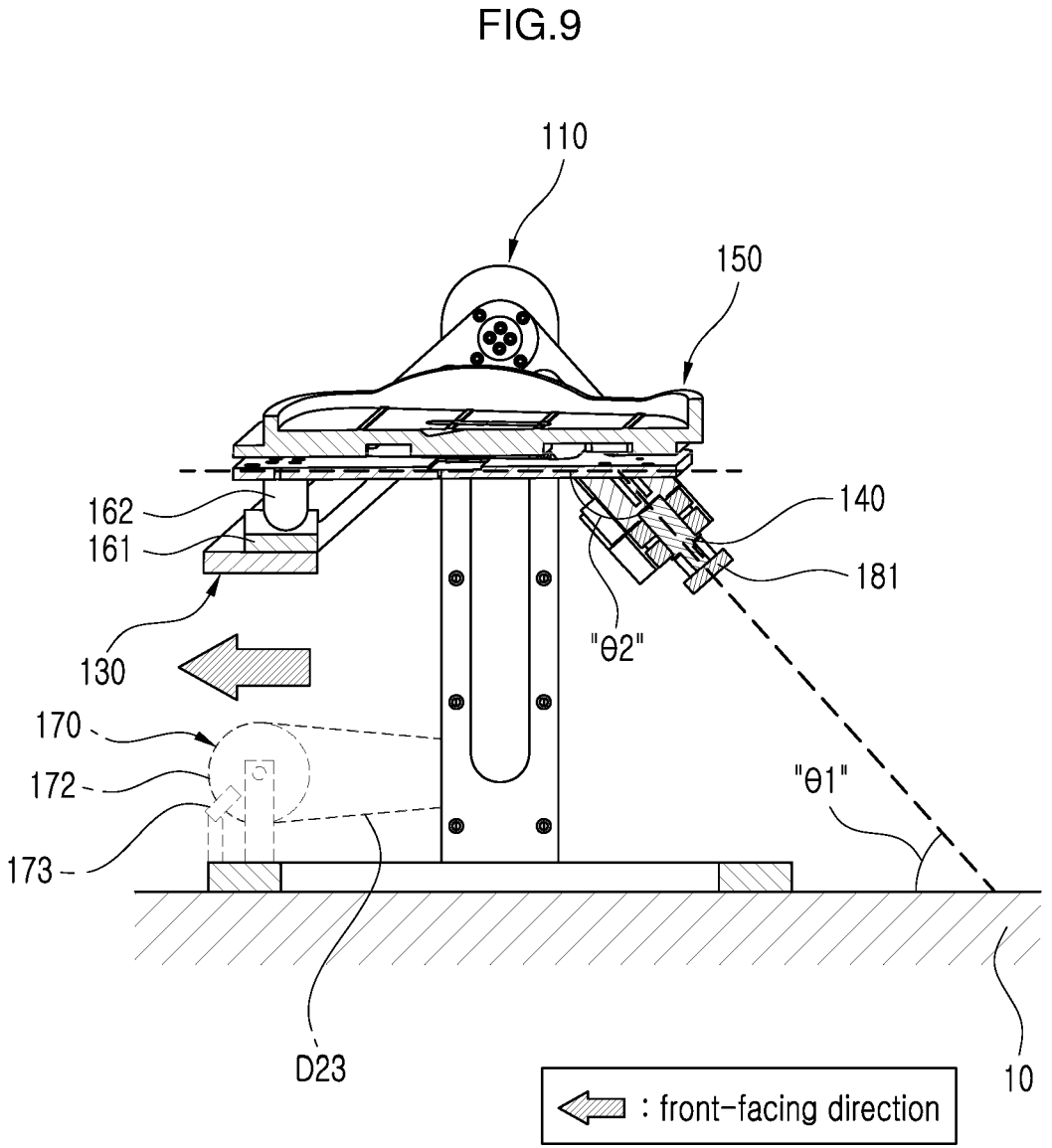
FIG. 9 is a cross-sectional view of the ankle movement providing device in FIG. 8 taken along line II-II.
Figure 10:
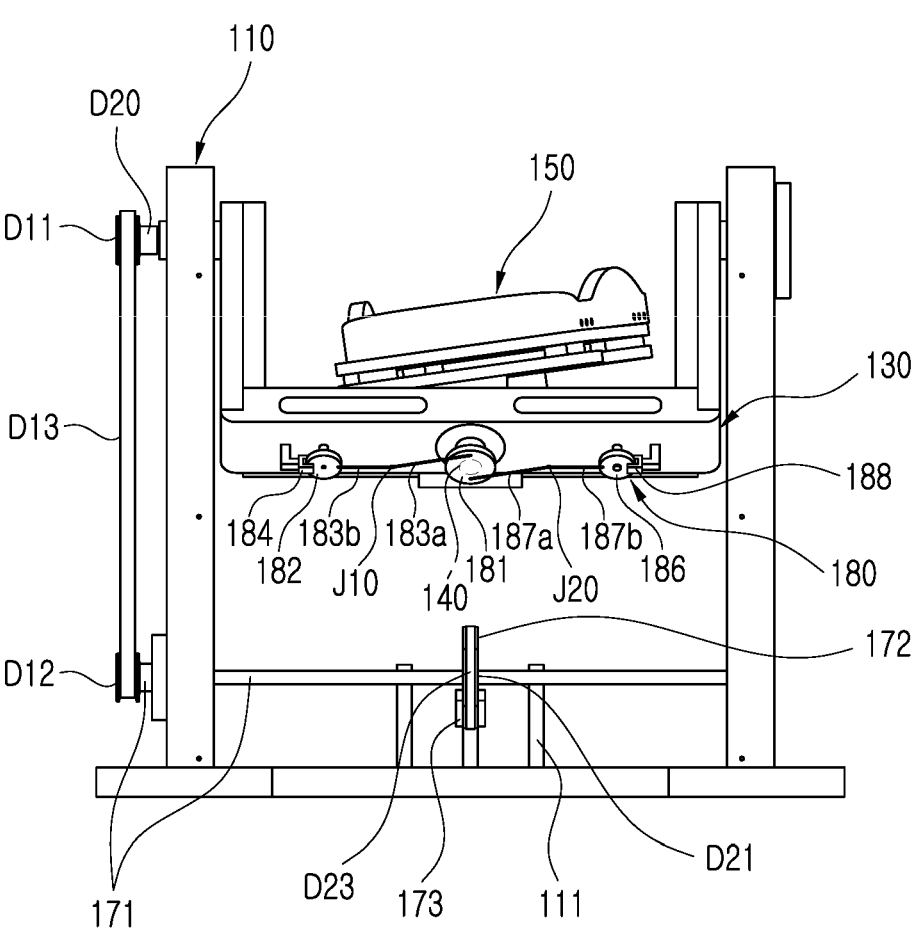
FIG. 10 is a rear view of the ankle movement providing device in FIG. 8.

FIG. 8 is a perspective view schematically illustrating an ankle movement providing device in an ankle muscle rehabilitation training apparatus according to an embodiment of the disclosure, FIG. 9 is a cross-sectional view of the ankle movement providing device in FIG. 8 taken along line II-II, and FIG. 10 is a rear view of the ankle movement providing device in FIG. 8.

The ankle movement providing device 100 according to an embodiment of the disclosure includes a support member 110, a first movement guide shaft 120, an intermediate member 130, a second movement guide shaft 140, and a foot support 150, as illustrated in FIGS. 8 to 10.

The support member 110 forms a framework of the ankle movement providing apparatus 100 according to the present disclosure, in which a lower portion is designed so as to be placed on a flat surface such as the ground (see 10 in FIG. 9), and upwardly protruding at both side portions thereof, as shown in FIGS. 8 to 10.

The first movement guiding shaft 120 serves as a hinge of the intermediate member 130 such that the intermediate member 130 is rotated with respect to the support member 110, and as shown in FIG. 8, may be positioned perpendicularly to the front-rear direction of the support member 110, and, as shown in FIGS. 8 and 9, positioned horizontally with respect to the ground (see 10 in FIG. 9). Therefore, the intermediate member 130 may perform a pitch motion with respect to the first movement guiding shaft 120.

In particular, the first movement guiding shaft 120 may be provided such that the ankle joint of the user is positioned in the axial direction thereof.

Accordingly, when the foot of the user is placed on the foot support 150 provided in the intermediate member 130 and rotated with respect to the first movement guiding shaft 120, the foot may be rotated upward (dorsiflexion) or downward (plantarflexion) with respect to the ankle joint, and accordingly, it is possible to assist rehabilitation of those who are unable to smoothly generate the ankle movements necessary for walking due to lower limb paralysis or muscle weakness, by inducing normal angle changes of the ankle with respect to the ankle joint as are generated during walking.

The intermediate member 130 is provided between the support member 110 and the foot support 150 and supports the foot support 150, in which, as shown in FIGS. 8 to 10, the intermediate member 130 is rotatably provided on the support member 110 with respect to the first movement guiding shaft 120 so as to be rotated together with the first movement guiding shaft 120, allowing a front portion of the foot to be rotated upward or downward with respect to the ankle joint.

The second movement guiding shaft 140 serves as a hinge of the foot support 150 such that the foot support 150 is rotated with respect to the intermediate member 130, and as shown in FIG. 9, may be positioned in parallel to the front-rear direction of the intermediate member 130 and positioned with an inclination with respect to the ground 10. Therefore, the intermediate member 130 may approximately perform a roll motion with respect to the first movement guiding shaft 120.

In particular, the second movement guiding shaft 140 may be provided such that the subtalar joint of the user is positioned in the axial direction thereof.

Accordingly, when the foot of the user is placed on the foot support 150 and rotated with respect to the second movement guiding shaft 140, the foot may be rotated left or right with respect to the subtalar joint, and accordingly, it is possible to assist rehabilitation of those who are unable to smoothly generate the ankle movements necessary for walking due to lower limb paralysis or muscle weakness by inducing normal angle changes of the ankle with respect to the subtalar joint as are generated during walking.

The foot support 150 is where the foot of the user is placed, and, as shown in FIG. 9, may be rotatably provided on the intermediate member 130 with respect to the second movement guiding shaft 140 and provided with an inclination with respect to the second movement guiding shaft 140.

In particular, as shown in FIG. 9, the second movement guiding shaft 140 may form an acute angle (01) with the ground 10 toward the front direction of the intermediate member 130, and the foot support may form an obtuse angle (02) with the second movement guiding shaft 140 toward the front direction of the intermediate member 130. Accordingly, through such inclined structures of the foot support 150 and the second movement guiding shaft 140, the subtalar joint of the foot of the user may be positioned in the axial direction of the second movement guiding shaft 140.

Furthermore, since the subtalar joint is positioned in the axial direction of the second movement guiding shaft 140, when the second movement guiding shaft 140 is rotated, the front end of the foot support 150 may be moved while following a left-and-right trajectory (T in FIG. 8). Specifically, the left-and-right trajectory T may be the trajectory in concave shape that gradually increases in height from its center towards the left and right sides. Therefore, it is possible to assist rehabilitation of those who are unable to smoothly generate the ankle movements necessary for walking due to lower limb paralysis or muscle weakness by inducing more stable angle changes of the ankle with respect to the subtalar joint as are generated during walking.

In addition, the ankle movement providing apparatus 100 according to the embodiment of the present disclosure described above may further include a left and right guide portion 160, as shown in FIG. 8.

The left and right guide portion 160 is a component that guides a front end of the foot support 150 in accordance with the left-and-right trajectory T while supporting the front end of the foot support 150. For example, the left and right guide portion 160 may include a driven guide member 161 and a driving guide member 162 as shown in FIG. 8. The driven guide member 161 is provided at a front end of the intermediate member 130 and has a concave shape corresponding to the left-and-right trajectory T, and the driving guide member 162 is provided to protrude from the front end of the foot support 150 and is moved while following the left-and-right trajectory T along the driven guide member 161.

Therefore, since a rear end of the foot support 150 is provided on the intermediate member 130 through the second movement guiding shaft 140, and the front end of the foot support 150 is supported by the intermediate member 130 through the left and right guide portion 160, the foot support 150 is supported at both the front end and the rear end thereof, such that the left and right movements of the foot support 150 can be more stably guided with a minimum operation error.

The first resistance force application part 170 is a component for improving the muscle strength of the ankle joint of the user by applying a load while the user is placing his or her foot on the foot support 150 and actively moving the ankle joint, and as shown in FIGS. 8 and 10, may be linked with the first movement guiding shaft 120 and apply a resistance force of an adjustable intensity against the active ankle movement of the user made with respect to the first movement guiding shaft 120.

For example, as shown in FIGS. 8 and 6, the first resistance force application part 170 may include a link shaft 171, a rotating disk 172, a first brake 173, and a first adjustment switch 174. The link shaft 171 may be rotatably provided on the support member 110 and linked with the first movement guiding shaft 120 through a first power transmission unit D10, and the rotating disk 172 may be rotatably provided on the support member 110 through a first support bracket 111 and linked with the first link shaft 171 through a second power transmission unit D20. The first brake 173 may apply a braking force to the rotating disk 172 using an electromagnet, and the first adjustment switch 174 may adjust the strength of the electromagnet of the first brake 173.

As shown in FIGS. 8 and 10, the first power transmission unit D10 may include a first pulley D11 provided on the first movement guiding shaft 120, a first pulley D12 provided on the link shaft 171, and a first belt D13 connecting the first and second pulleys D11 and D12. As another example, although not shown, the first power transmission unit may have a sprocket-chain structure, or a gear assembly structure in which a plurality of gears are engaged.

In addition, as shown in FIG. 8, the second power transmission unit D20 may include a third pulley D21 provided on the link shaft 171, a fourth pulley D22 provided on an outer peripheral surface of the rotating disk 172, and a second belt D23 connecting the third and fourth pulleys D21 and D22. As another example, although not shown, the second power transmission unit may have a sprocket-chain structure, or a gear assembly structure in which a plurality of gears are engaged.

In addition, as shown in FIG. 8, an one-way bearing 175 may be provided between the link shaft 171 and the third pulley D21 such that resistance force is applied only when the foot support 150 is pressed with the ankle of the user. As another example, although not shown, such an one-way bearing may be provided between the first movement guiding shaft 120 and the first pulley D11, and provided between the rotating disk 172 and a shaft of the first support bracket 111.

Although the present invention has been described in connection with some examples herein, the present invention should not be limited to those examples only, and various other changes and modifications made by those skilled in the art from the basic concept of the disclosure are also within the scope of the claims appended herein.

The invention claimed is:

1. An electrical stimulation-based ankle muscle rehabilitation training apparatus, comprising:
   a functional biaxial ankle movement providing device (100) that provides dorsiflexion, plantar flexion, eversion and inversion, and pronation and supination operations;
   first and second electrode pads (P1, P2) configured to be attached to an ankle dorsiflexor, respectively;

third and fourth electrode pads (P3, P4) configured to be attached to an ankle evertor, respectively;

an electrical stimulation providing unit for applying electrical stimulation to the first to fourth electrode pads; and a control unit that controls the ankle movement providing device to sequentially perform a first operation of repeating dorsiflexion and plantarflexion movements a plurality of times, a second operation of repeating eversion and inversion movements a plurality of times, and a third operation of repeating supination and pronation movements a plurality of times, and controls the electrical stimulation providing unit to apply electrical stimulation to the first to fourth electrode pads.

2. The apparatus of claim 1, wherein the first and second electrode pads (P1, P2) are configured to be attached to proximal and distal portions of the ankle dorsiflexor, respectively, and the third and fourth electrode pads (P3, P4) are configured to be attached to proximal and distal portions of the ankle evertor, respectively.

3. The apparatus of claim 1, wherein the control unit controls so as to:

apply electrical stimulation to the first and second electrode pads (P1, P2) when the dorsiflexion movement occurs during the first operation;

apply electrical stimulation to the third and fourth electrode pads (P3, P4) when the inversion movement occurs during the second operation; and apply electrical stimulation to the first to fourth electrode pads (P1, P2, P3, P4) when the supination movement occurs during the third operation.

4. The apparatus of claim 3, wherein the control unit controls so as to apply electrical stimulation to none of the first to fourth electrode pads when the plantar flexion movement occurs during the first operation, when the eversion movement occurs during the second operation, and when the pronation movement occurs during the third operation.

5. The apparatus of claim 1, wherein the control unit controls the ankle movement providing device such that the first operation repeats the dorsiflexion and plantar flexion movements 20 times in sequence, the second operation repeats the eversion and inversion movements 20 times in sequence, and the third operation repeats the supination and pronation movements 40 times in sequence.

6. The apparatus of claim 5, wherein each of the dorsiflexion, plantar flexion, eversion, inversion, supination, and pronation operations is performed at a slow speed in consideration of occurrence of speed-dependent spasticity, time required for one operation of the dorsiflexion movement is 10 to 12 seconds, and time required for one operation of each of the plantar flexion, eversion, inversion, supination and pronation movements is 10 to 15 seconds.

7. An ankle muscle rehabilitation training control method using an ankle movement providing device (100), first and second electrode pads (P1, P2), and third and fourth electrode pads (P3, P4), the method comprising:

attaching the first and second electrode pads (P1, P2) to proximal and distal portions of an ankle dorsiflexor, respectively;

attaching the third and fourth electrode pads (P3, P4) to proximal and distal portions of an ankle evertor, respectively;

using the ankle movement providing device, sequentially providing a first operation of repeating dorsiflexion and plantar flexion movements a plurality of times, a second operation of repeating eversion and inversion movements a plurality of times, and a third operation of repeating supination and pronation movements a plurality of times; and by the first to fourth electrode pads, applying electrical stimulation.

8. The method of claim 7, wherein the first operation repeats the dorsiflexion and plantar flexion movements 20 times in sequence, the second operation repeats the eversion and inversion movements 20 times in sequence, and the third operation repeats the supination and pronation movements 40 times in sequence.

9. The method of claim 8, wherein each of the dorsiflexion, plantar flexion, eversion, inversion, supination, and pronation operations is performed at a slow speed in consideration of occurrence of speed-dependent spasticity, time required for one operation of the dorsiflexion movement is 10 to 12 seconds, and time required for one operation of each of the plantar flexion, eversion, inversion, supination, and pronation movements is 10 to 15 seconds.

* * * * *